United States Patent [19]

Perner et al.

[11] 4,200,733

[45] Apr. 29, 1980

[54] IODINE-CONTAINING BLOCK COPOLYMERS OF 1,4-BUTYLENE OXIDE AND ETHYLENE OXIDE

[75] Inventors: Johannes Perner, Neustadt; Norbert Greif, Bobenheim; Rolf Fikentscher, Ludwigshafen; Paul Diessel, Mannheim, all of Fed. Rep. of Germany

[73] Assignee: BASF Aktiengesellschaft, Fed. Rep. of Germany

[21] Appl. No.: 25,174

[22] Filed: Mar. 29, 1979

[30] Foreign Application Priority Data

Apr. 22, 1978 [DE] Fed. Rep. of Germany ....... 2817785

[51] Int. Cl.² ...................... C08L 71/02; C08G 65/32
[52] U.S. Cl. .................................... 528/417; 252/106; 525/409; 568/614
[58] Field of Search ........................... 260/823; 526/1; 568/614; 528/417, 404; 252/106

[56] References Cited

U.S. PATENT DOCUMENTS

| | | | |
|---|---|---|---|
| 1,970,578 | 8/1934 | Schoeller et al. ....................... | 260/98 |
| 2,213,477 | 9/1940 | Steindorff et al. .................... | 260/613 |
| 3,285,816 | 11/1966 | Kaplan et al. .......................... | 167/70 |
| 3,438,906 | 4/1969 | Duvall .................................... | 252/106 |

*Primary Examiner*—Earl A. Nielsen
*Attorney, Agent, or Firm*—Keil & Witherspoon

[57] ABSTRACT

Iodine-containing block copolymers which contain from 5 to 25% by weight of bonded iodine, and which are based on iodine-free compounds of the formula I $$R(AB)_z \qquad \qquad I$$

where
if $z=1$, R is hydrogen or a $C_1$–$C_{18}$-aliphatic hydrocarbon radical,
if $z \neq 1$, R is a z-valent aliphatic hydrocarbon radical of 2 to 8 carbon atoms, which may or may not carry up to z ethylene oxide units,
z is from 1 to 6,
A is a polymer or copolymer block of from 4 to 100 1,4-butylene oxide units and from 0 to 25 ethylene oxide units and
B is a polymer or copolymer block of from 0 to 50 1,4-butylene oxide units and from 1 to 100 ethylene oxide units, the proportion of 1,4-butylene oxide being >50 mole % in A and <50 mole % in B.

3 Claims, No Drawings

IODINE-CONTAINING BLOCK COPOLYMERS OF 1,4-BUTYLENE OXIDE AND ETHYLENE OXIDE

Iodine-containing polymers which contain ethylene oxide units and propylene oxide units (and which are referred to as iodophores) are known as active ingredients in disinfectant cleansers which are used, for example, in the beverage industry and in agriculture (dairies).

U.S. Pat. Nos. 1,970,578, 2,213,477 and 3,438,906 describe such iodine-containing ethylene oxide/propylene oxide polymers as being, for example, disinfectant components in cleansers, and allegedly possessing a low foaming power. A disadvantage of these materials is, however, that they cannot be satisfactorily diluted to ready-to-use concentrations of from about 50 to 2,000 ppm, since a precipitate or turbidity often results, which in most cases is attributable to elementary iodine and which greatly reduces the activity of the agents.

It is an object of the present invention to provide iodophores which can be diluted adequately, without showing the stated disadvantages, and which can therefore be stored virtually indefinitely at the ready-to-use concentrations.

We have found that this object is achieved with novel iodine-containing block copolymers which contain 1,4-butylene oxide—hereinafter also commonly referred to as tetrahydrofuran (THF)—as the comonomer, and which are defined in the appended claims.

A series of iodine-free copolymers of similar structure has long been known, for example from German Pat. Nos. 741,478, 766,208 and 1,120,139 where they are recommended as, for example, lubricating oil additives.

In the present case, the iodine-free compounds on which the iodophores are based are block copolymers of THF and ethylene oxide, which are either used per se (R=H) or as an adduct with monohydric or polyhydric alcohols in accordance with the remaining definitions of R in formula I.

The process of preparation of the block copolymers is simple and is based on the following starting materials:

1. Alcohols of the formula $R(OH)_z$, where R and z are as defined in formula I, except that R is not hydrogen.

These alcohols include monohydric aliphatic alcohols of 1 to 18 carbon atoms, eg. methanol, ethanol, propanols, butanols, pentanols, n-hexanol, octanols, eg. 2-ethyl hexanol, n-nonanol, n-decanol, n-dodecanol and stearyl alcohol, as well as mixtures of these, and mixtures of synthetic aliphatic alcohols, eg. oxo-alcohols or Ziegler alcohols of the $C_9/C_{11}$-, $C_{11}/C_{13}$-, $C_{13}/C_{15}$-, $C_{15}/C_{17}$-, $C_{12}$-$C_{14}$- or $C_{14}$-$C_{16}$-fractions.

Suitable polyhydric alcohols ($z \neq 1$, ie. from 2 to 6) are the conventional types where the hydrocarbon radical is of 2 to 8 carbon atoms.

Examples to be mentioned particularly are ethylene glycol, 1,2- and 1,3-propylene glycol, 1,4-butanediol, pentitols and hexitols, eg. sorbitol, glycerol, trimethylolpropane and pentaerythritol.

2. Tetrahydrofuran and ethylene oxide.

The latter two are the sole starting materials if, in formula I, R is hydrogen.

The preparation is carried out by first forming an adduct of one of the said alcohols with, per OH group, a mixture of from 4 to 100 moles of tetrahydrofuran, preferably from 4 to 50 moles, and from 0 to 25 moles of ethylene oxide, in accordance with the definition of A in formula I, in the presence of a Lewis acid, eg. $BF_3$-etherate, $AlCl_3$, $ZnCl_2$ and the like, at from 0° to 100° C.; thereafter the product is reacted with, per OH group, from 0 to 50, preferably from 0 to 25, moles of THF mixed with from 1 to 100, preferably from 1 to 50, moles of ethylene oxide, in accordance with the definition of B, in the presence of the same catalysts and at the same temperatures. THF is used in excess in the first stage and ethylene oxide in excess in the second stage. In accordance with the definition, adducts of pure THF-ethylene oxide block polymers, which can also be prepared with alkaline catalysis, are in principle also active.

If it is not desired to prepare adducts with alcohols (R=H), then THF alone, or THF and ethylene oxide are first polymerized (to form A in formula I) in the presence of the above Lewis acids, and thereafter, as stated above, the components of block B, ie. ethylene oxide alone or mixed with THF, are reacted with the product at from 20° to 80°. Where ethylene oxide alone is used, the reaction can also be catalyzed by alkalis, eg. NaOH or $NaOCH_3$, at 60°–120°.

Within the limits given in the definition, it is particularly advantageous if the preparation is carried out with an overall molar ratio of THF to ethylene oxide of from 0.25:1 to 1.2:1.

The products may be characterized by the OH number and the molecular weight. The resulting iodine-free block copolymers, which are used, depending on their state of aggregation, either undiluted or dissolved in a greater or lesser amount of water, are treated with an amount of elementary iodine which is such that the end product contains from 5 to 25, preferably from 10 to 20, % by weight of bonded iodine.

This operation is effected by simply stirring the iodine into the liquid product or its aqueous solution.

The iodine content can be determined in the conventional manner by titration with thiosulfate solution and starch indicator in dilute aqueous solution.

The iodophores obtained can be used as active ingredients in disinfectant cleansers, for example in the beverage industry and in agriculture (dairies).

The Examples which follow show the excellent shelf life of even very dilute products, when compared with conventional known products. The preparation of the THF-ethylene oxide polymers is conventional and therefore does not require more detailed explanation. The iodophore is prepared by stirring iodine, at room temperature, into the polymer, which in most cases is liquid, and continuing to stir for from 30 to 60 minutes.

The products shown below were tested by this method.

The following abbreviations are used:
THF=tetrahydrofuran
EO=ethylene oxide
MW=molecular weight An oblique stroke denotes a mixed block and a hyphen denotes a block copolymer.

| | | |
|---|---|---|
| $x$ | = number of THF units | in block A |
| $y$ | = number of EO units | |
| $x'$ | = number of THF units | in block B |
| $y'$ | = number of EO units | |

| Ex. No. | Product | OH number | I (% by weight) |
|---|---|---|---|
| 1 | $THF_{23.2}/EO_{5.2}\text{-}(EO)_{17.8}$ | 42 | 20 |
| 2 | $THF_{26.1}/EO_{6.35}\text{-}(EO)_{23.1}$ | 35 | 20 |
| 3 | $THF_{26.1}/EO_{6.35}\text{-}(EO)_{17.2}$ | 39 | 20 |
| 4 | $C_9/C_{11}$-Oxo-alcohol + $THF_{4.9}/EO_{5.9}\text{-}(EO)_{9.3}$ | 49 | 20 |
| 5 | Butanediol + $(THF)_{12.5}/(EO)_{7.6}\text{-}(EO)_{15.0}$ | 57 | 20 |
| 6 | Butanediol + $(THF)_{22.0}/(EO)_{8.0}\text{-}(EO)_{24.0}$ | 60 | 20 |
| 7 | $(THF)_{13.8}\text{-}(EO)_{12.2}$ | 75 | 20 |
| 8 | $(THF)_{26.0}\text{-}(EO)_{20.4}$ | 39 | 20 |
| 9 | Sorbitol + $(THF)_{41}/(EO)_{20}\text{-}(EO)_{41.4}$ | 41.4 | 20 |

| Comparative example (PO = propylene oxide) | | |
|---|---|---|
| (a) EO/PO 30:70 | 1100 | 20 |
| (b) EO/PO 20:80 | 2500 | 20 |
| (c) Nonylphenol + 15 EO | — | 20 |
| (d) 1 Hydroxyheptadecenylimidazole + 20 EO + 6 PO | — | 20 |

The Tables which follow show the stability characteristics of dilute solutions (iodine content less than 2% by weight) and the foaming power.

TABLE 1

Stability characteristics of dilute aqueous solutions of THF-EO block polymers + iodine

| | Iodine content in % | | | | |
|---|---|---|---|---|---|
| Ex. No. | immediately | after 1 day | after 1 week | after 2 weeks | after 4 weeks |
| 1 | 1.69 | 1.68 | 1.68 | 1.68 | 1.68 |
| 2 | 1.68 | 1.68 | 1.68 | 1.68 | 1.67 |
| 3 | 1.67 | 1.67 | 1.67 | 1.67 | 1.67 |
| 4 | 1.54 | 1.54 | 1.54 | 1.54 | 1.53 |
| 5 | 1.71 | 1.71 | 1.71 | 1.70 | 1.69 |
| 6 | 1.86 | 1.86 | 1.85 | 1.85 | 1.84 |
| 7 | 1.84 | 1.84 | 1.82 | 1.80 | 1.80 |
| 8 | 1.80 | 1.80 | 1.80 | 1.79 | 1.79 |
| 9 | 1.70 | 1.70 | 1.70 | 1.70 | 1.69 |
| a | 1.64 | 1.50 | has precipitated | | |
| b | 1.57 | has precipitated | | | |
| c | 1.91 | 1.88 | 1.80 | 1.79 | 1.75 |
| d | 1.63 | 1.60 | 1.38 | 0.99 | 0.94 |

TABLE 2

Foaming characteristics of dilute aqueous solutions of THF-EO block polymers + iodine
Foam-beating method according to DIN 53,902, sheet 1
2 g/l, room temperature, tap water of 16° German hardness

| | Foam volume in ml | | | |
|---|---|---|---|---|
| Ex. No. | immediately | after 1 minute | after 3 minutes | appearance of the solutions |
| 1 | 400 | 260 | 160 | clear |
| 2 | 420 | 300 | 160 | clear |
| 3 | 400 | 250 | 200 | clear |
| 4 | 430 | 300 | 260 | clear |
| 5 | 430 | 260 | 90 | cloudy |
| 6 | 400 | 250 | 160 | clear |
| 7 | 250 | 170 | 60 | clear |
| 8 | 260 | 100 | 60 | clear |
| 9 | 360 | 220 | 130 | clear |
| a | 470 | 310 | 260 | very cloudy |
| b | 400 | 200 | 180 | has precipitated |
| c | 460 | 260 | 210 | clear |
| d | 420 | 260 | 180 | clear |

We claim:

1. An iodine-containing block copolymer which contains from 5 to 25% by weight of bonded iodine, which is combined with an iodine-free compound of the formula I $$R(AB)_z \qquad I$$

where
- if $z=1$, R is hydrogen or a $C_1\text{-}C_{18}$-aliphatic hydrocarbon radical,
- if $z \neq 1$, R is a z-valent aliphatic hydrocarbon radical of 2 to 8 carbon atoms, or a divalent aliphatic hydrocarbon radical of 2 to 8 carbon atoms which carries up to z ethylene oxide units,
- z is from 1 to 6,
- A is a polymer or copolymer block of from 4 to 100 1,4-butylene oxide units and from 0 to 25 ethylene oxide units and
- B is a polymer or copolymer block of from 0 to 50 1,4-butylene oxide units and from 1 to 100 ethylene oxide units, the proportion of 1,4-butylene oxide being > 50 mole % in A and < 50 mole % in B.

2. A block copolymer as claimed in claim 1, wherein the overall molar ratio of 1,4-butylene oxide units to ethylene oxide units is from 0.25:1 to 1.2:1.

3. A process for the preparation of an iodine-containing block copolymer as claimed in claim 1, wherein a compound of the formula I is combined with an amount of elementary iodine which is such that the reaction product contains from 5 to 25% by weight of bonded iodine, based on the reaction product.

* * * * *